United States Patent [19]

Knox et al.

[11] Patent Number: 4,610,684

[45] Date of Patent: Sep. 9, 1986

[54] FLEXIBLE CONTAINER AND MIXING SYSTEM FOR STORING AND PREPARING I.V. FLUIDS

[75] Inventors: Kenneth H. Knox, Vernon Hills; Mark E. Larkin, Lindenhurst, both of Ill.

[73] Assignee: Abbott Laboratories, North Chicago, Ill.

[21] Appl. No.: 623,065

[22] Filed: Jun. 22, 1984

[51] Int. Cl.4 .............................................. A61B 19/00
[52] U.S. Cl. ..................................................... 604/416
[58] Field of Search ........................ 604/89, 90, 91, 87, 604/416, 410

[56] References Cited

U.S. PATENT DOCUMENTS 806,090 12/1905 Allenberg .
2,176,923 10/1939 Nitardy .
3,290,017 12/1966 Davies et al. .
3,532,254 10/1970 Burke .
3,608,709 9/1971 Pike .
3,696,919 10/1972 Miles .................................. 604/416
4,198,972 4/1980 Herb .
4,396,383 8/1983 Hart .................................. 604/416
4,410,321 10/1983 Pearson et al. ..................... 604/416
4,458,811 7/1984 Wilkinson .
4,465,488 8/1984 Richmond et al. .
4,467,588 8/1984 Carveth .
4,484,920 11/1984 Kaufman et al. .................. 604/416

FOREIGN PATENT DOCUMENTS 894727 10/1982 Belgium .
1486622 7/1969 Fed. Rep. of Germany .
1180102 6/1959 France .
94886 1/1970 France .
364073 10/1962 Switzerland .

*Primary Examiner*—John D. Yasko
*Attorney, Agent, or Firm*—Robert W. Stevenson; Alan R. Thiele; Martin L. Katz

[57] ABSTRACT

A stoppered vial containing a medicament to be mixed with a diluent is enclosed within a flexible I.V. fluid container. Mixing of the medicament in the stoppered vial with a diluent also contained within the flexible I.V. fluid container is accomplished by first, unstoppering the vial by manipulation of the flexible sides of the container; then second, causing the fluid to intermix with the medicament in the vial by compressing that portion of the flexible container holding the diluent.

17 Claims, 8 Drawing Figures

FLEXIBLE CONTAINER AND MIXING SYSTEM FOR STORING AND PREPARING I.V. FLUIDS

BACKGROUND OF THE INVENTION

This invention relates to a manually operable flexible container system which includes means to intermix a medicament and a diluent entirely within the container by physical manipulation from outside the container. More particularly, this invention relates to an additive mixing system for use in the infusion of I.V. fluids. The mixing system is made part of a flexible storage container commonly used to hold a standard liquid diluent such as normal saline solution, dextrose or water. The additive is commonly a powdered or liquid medicament which is compatible with the liquid diluent for treatment purposes but cannot be stored in solution with the liquid diluent for long periods of time.

Container devices which provide separate spaces in a single unit for separately enclosing different materials in such a way that they may be intermixed at time of use are described in U.S. Pat. No. 2,176,923 to Nitardy, U.S. Pat. No. 3,290,017 to Davies, et al., and U.S. Pat. No. 3,532,254 to Burke, et al. These container devices are deficient because they do not maintain an effective fluid-tight seal or moisture barrier between the two spaces containing the incompatible materials which are eventually to be intermixed. This deficiency is caused by the various barriers between the storage spaces within the container not adequately withstanding the normal rigors of packaging, handling and shipping. If the fluid-tight seal or moisture barrier between the storage spaces is in any way ruptured, premature mixing of the materials may occur which then renders the materials ineffective for eventual use. Additionally, for containers used in health care situations, sterility of the materials to be mixed and the mixing system itself must be strictly maintained. If more complexity is added to the container to assure a fluid-tight seal or moisture barrier between the storage spaces, sequential sterilization of the mixing system during the various stages of manufacture may become difficult and expensive. One solution is to manufacture and fill the container in a sterile environment. Such manufacture however, is expensive. Consequently, the need exists in the art to provide a container device which will provide a fluid-tight seal and an impervious moisture barrier between a powdered medicament and a liquid diluent that can both be easily sterilized during manufacture and conveniently used as part of an I.V. administration system.

The prior art does not show the use of a vial with a removable stopper or stoppers within a flexible container to maintain a fluid-tight and moisture-proof barrier in a sterile environment before fluid communication between the contents of the vial and the liquid diluent is established.

It is therefore an advantage of the present invention to provide a manually operable, flexible container and mixing system, not subject to the aforementioned limitations and disadvantages of the prior art.

It is another advantage of the present invention to provide a manually operable flexible container that is substantially chemically inert, nonbreakable, lightweight, and exceedingly compact.

It is still another advantage of the present container and mixing system to provide a manually operable, flexible container that is easily activated, and does not require special sealing gaskets or "O" rings. Other advantages of the present invention will become more apparent in the following description.

Summary of the Invention

The container device of the present invention provides a system for separately storing and subsequently mixing a medicament and a diluent in a sterile environment for use in an I.V. administration system. The container is a sealed flexible bag or pouch with access ports mandrel sealed on its edge. In the preferred embodiment a dividing partition in the form of a seal with integral weakened sections spans the interior of the container and separates it into two separate compartments for storing and isolating the materials before mixing. A first compartment within the flexible container contains fluid, typically a liquid diluent commonly used in I.V. applications. The second compartment contains a stoppered vial which is used for storing a powdered or liquid medicament. When it is desired to mix the liquid diluent contents of the first compartment within the flexible container and the powdered medicament contents of the stoppered vial, the two stoppers are removed from the ends of the vial by direct manipulation of the removable stoppers through the flexible sides of the container. The walls of the flexible container are then compressed or squeezed so that hydraulic forces generated within the liquid diluent will cause the weakened section of the dividing seal between the compartments to break, thus permitting flow between the first compartment and the second compartment of the flexible container. The liquid diluent in the first compartment may then be mixed with the powdered medicament in the vial by utilizing the flexibility of the container to agitate the diluent-medicament mixture. The diluent-medicament mixture is dispensed from the container by connecting a fluid administration system to the access ports of the container.

DESCRIPTION OF THE DRAWINGS

A better understanding of the manually operated flexible container and mixing system of this invention will be had by reference to the drawings wherein.

DESCRIPTION OF THE PREFERRED EMBODIMENT

Figure 2:
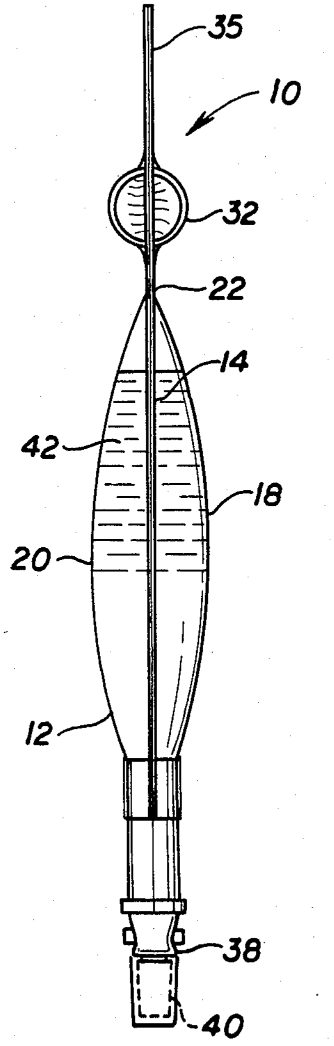
FIG. 2 is a view in side elevation of the flexible container and mixing system shown in FIG. 1.
Figure 1:
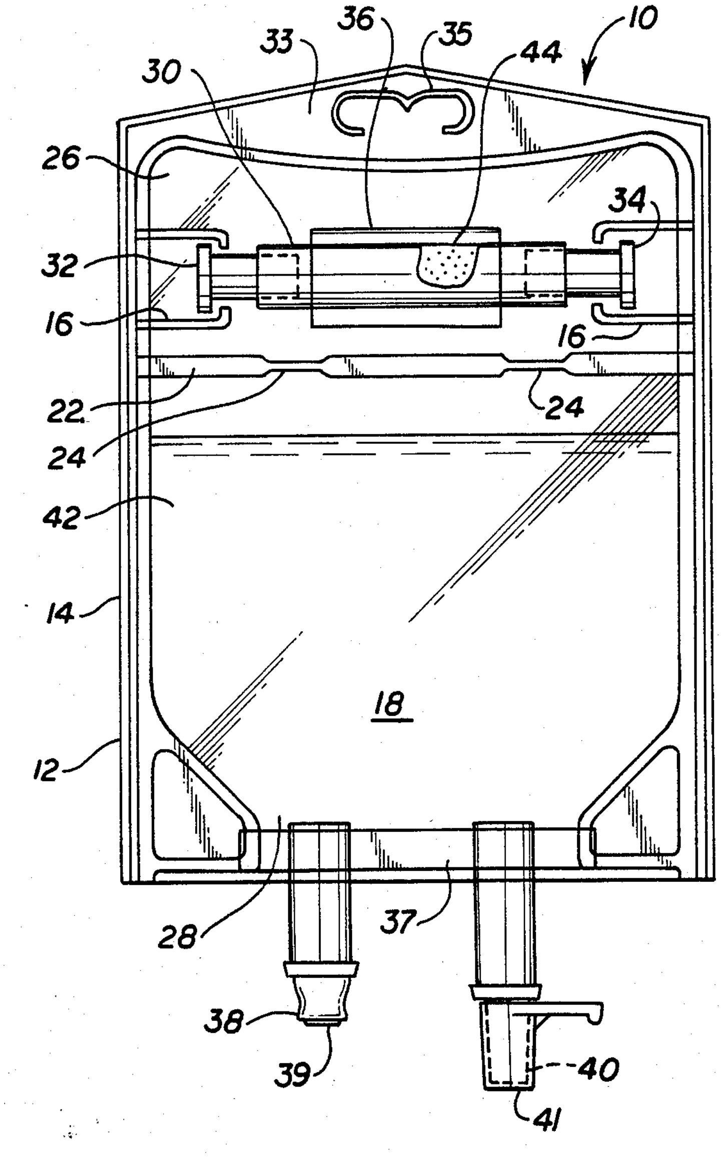
FIG. 1 is a view in front elevation of the flexible container and mixing system of this invention.

Proceeding to a detailed description of the preferred embodiment of the invention, FIGS. 1 and 2 show a manually operable dual compartmented container and mixing system, generally 10, of this invention. The device 10 is characterized by having a flexible outer container 12 formed from two sheets 18 and 20 of a flexible thermoplastic material which are then joined at their respective perimeters to form an edge 14. At the top of flexible container 12 a hanger portion 35 is formed in top seal 33. Administration port 40 and additive port 38 are mandrel sealed at 37 within edge 14 at the bottom of flexible container 12. Additive port 38 is adapted for the use of a syringe to add components through a rubber reseal 39 and administration port 40 with cap 41 may be used to connect the container and mixing system 10 to an intravenous administration system by use of a piercing pin (not shown) once cap 41 has been removed. Flexible outer container 12 is divided into two internal compartments 26 and 28 by container dividing partition 22. Within container dividing partition 22 are shown two weakened sections 24. Typically contained within first compartment 28 will be liquid diluent 42. A dual stoppered vial 30 is enclosed within second compartment 26. While vial 30 with two stoppers 32 and 34 is shown it will be understood that a vial designed to employ a plurality of stoppers may be used. Typically a powdered medicament 44 is contained within vial 30. Optionally, dual stoppered vial 30 may be secured against the side of compartment 26 by a retainer 36. Retainer 36 may be a piece of flexible thermoplastic material which is attached to the inside of thermoplastic sheet 18 forming one wall of second compartment 26. In FIG. 1, stoppers 32 and 34 are shown as being further secured into place by U-shaped seals 16 formed in second compartment 26. U-shaped seals 16 are formed by using a die piece on either side of stoppers 32 and 34 to cause thermoplastic sheets 18 and 20 to fuse to each other around stoppers 32 and 34. It will be understood that stoppers 32 and 34 need not be secured within U-shaped seals 16 in order to be manipulable from the outside of container 12.

Figure 6:
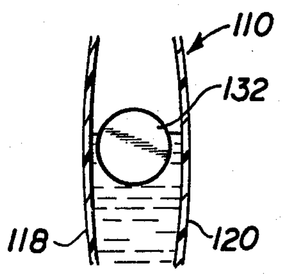
FIG. 6 is a view taken along line 6—6 of the flexible container and mixing system shown in FIG. 5.
Figure 5:
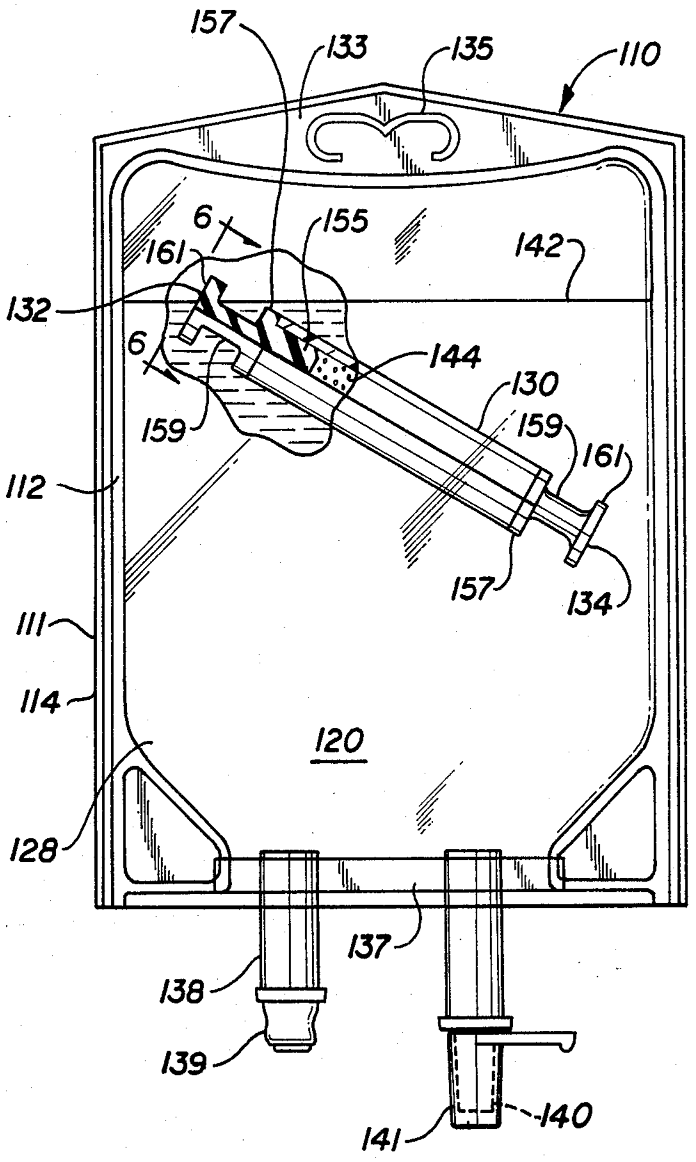
FIG. 5 is a view in front elevation of first alternative embodiment of the flexible container and mixing system.

In FIGS. 5 and 6, a first alternative embodiment of the device of this invention, generally 110 is shown, wherein the same reference characters in the "100" series of numbers have been employed to designate parts having the same general function, construction and relative location as in the preferred embodiment. Herein, vial 130 containing powdered medicament 144 is suspended in liquid diluent 142. Stoppers 132 and 134 in vial 130 prevent moisture from entering vial 130. Specifically stoppers 132 and 134 include an insert portion 155 which seals against the inside of vial 130. Flange portion 157 seals against the end of vial 130 and stem 159 and outer flange 161 provide surfaces for grasping stoppers 132 and 134. As in the preferred embodiment ports 128 and 140 may be mandrel sealed as at 137 in the edge 114 of container 112.

Figure 7:
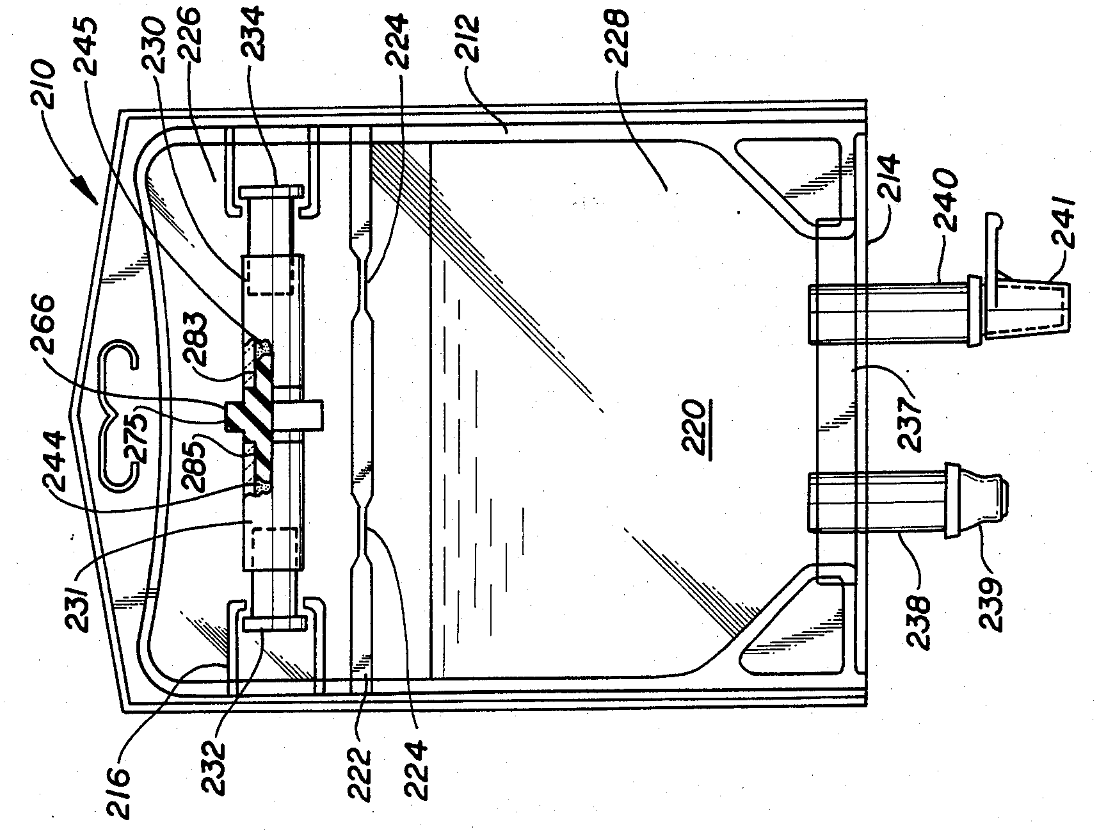
FIG. 7 is a view in front elevation of a second alternative embodiment of the flexible container and mixing system.

In FIG. 7 a second alternative embodiment, generally 210 of the device is shown, wherein the same reference characters in the "200" series of numbers have been employed to designate parts having the same general function, construction and relative location as in the preferred embodiment. Herein, vial sections 230 and 231 are joined together by stopper 266. Stopper 266 consists of insert portions 283 and 285 which seal against the inside of vial sections 230 and 231 and a central flange 275 which seals against the ends of vial sections 230 and 231. Two separate medicaments 244 and 245 are contained one within each vial section 230, 231. The complete vial assembly consisting of sections 230 and 231 and stoppers 232, 266 and 234 is contained within second compartment 226 of flexible container 212. As in the peferred embodiment, a partition 222 with weakened portions 224 divides the container 212 into two compartments 226 and 228. As in the preferred embodiment, ports 238 and 240 may be mandrel sealed 237 in the edge 214 of container 212.

Figure 8:
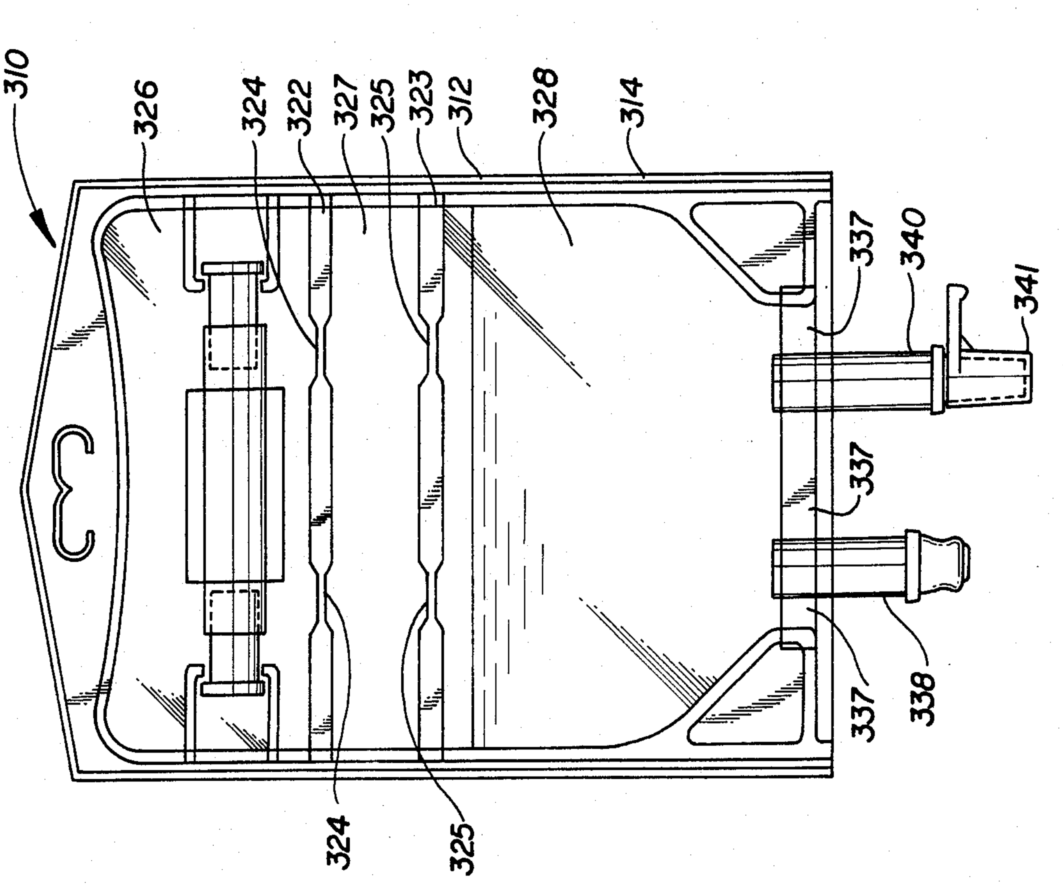
FIG. 8 is a view in front elevation of a third alternative embodiment of the flexible container and mixing system.

A third alternative embodiment generally 310 is shown in FIG. 8, wherein the same reference characters in the "300" series of numbers have been employed to designate parts having the same general function, construction and relative location as in the preferred embodiment. Herein a neutral or test zone 327 is formed between first compartment 328 and second compartment 326. This neutral or test zone 327 is formed by adding a second container dividing partition 323 with weakened sections 325 spanning container 312. As in the preferred embodiment, an additive port 338 and administration port 340 may be mandrel sealed 337 within the edge 314 of container 312.

OPERATION

Figure 3:
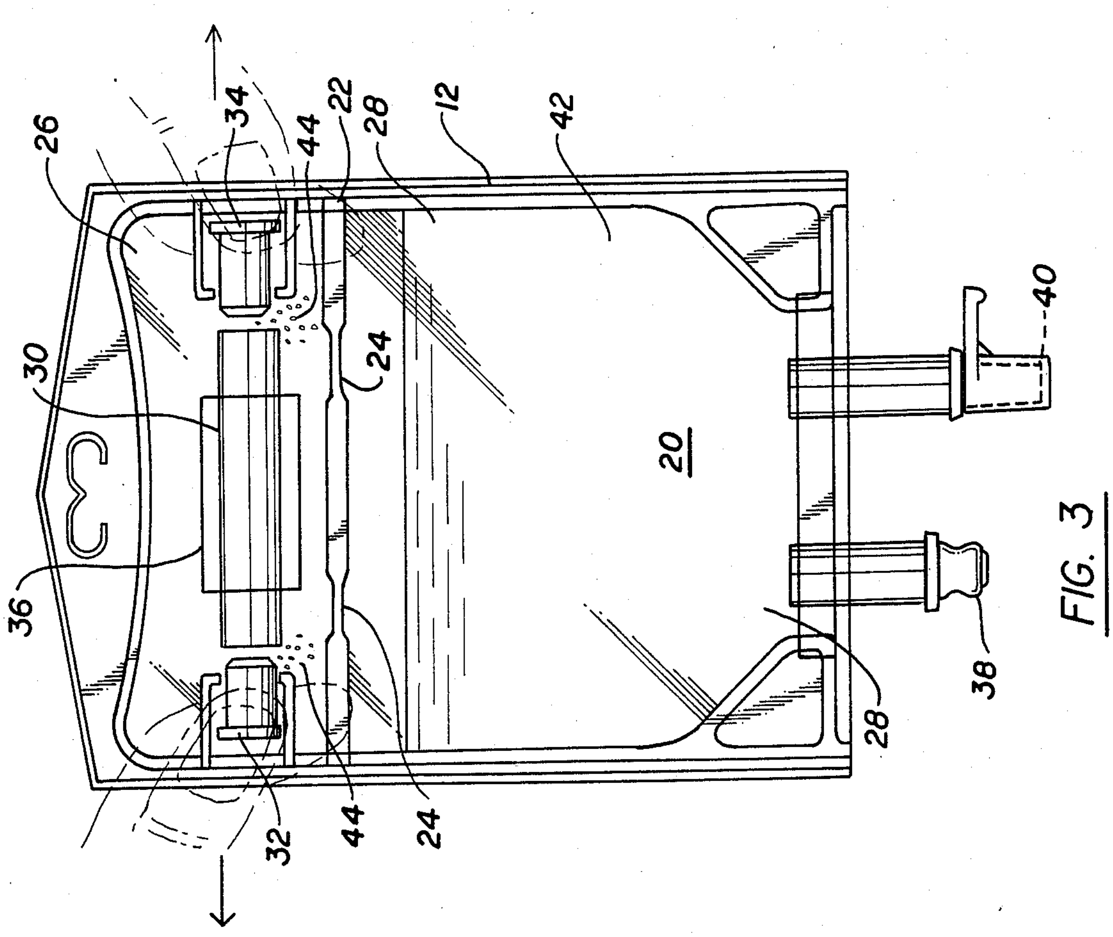
FIG. 3 is a view similar to FIG. 1 illustrating initiation of the mixing function of the flexible container and mixing system of this invention.
Figure 4:
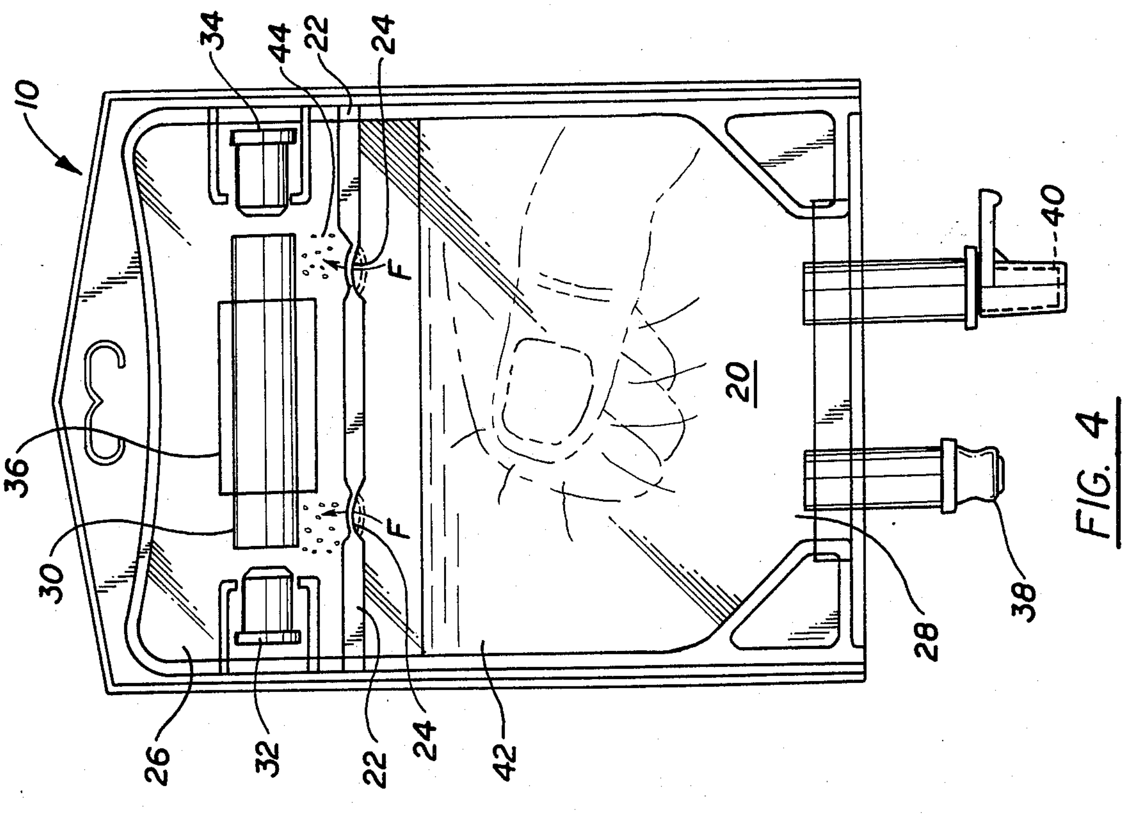
FIG. 4 is a view similar to FIG. 1 illustrating completion of the mixing function flexible container and mixing system of this invention.

A better understanding of the advantages of the manually operable dual compartmented container 10 will be had by a description of its operation. The dual compartmented container and mixing system 10 will be received by health care personnel generally as shown in FIGS. 1 and 2. Activation of the container and mixing system 10 is begun by grasping and pulling stoppers 32 and 34 away from vial 30 utilizing the flexible wall properties of container 12 as shown in FIG. 3. Once stoppers 32 and 34 have been removed from dual stoppered vial 30, first compartment 28 is manipulated by compressing walls 18 and 20 so as to cause the hydraulic forces developed within liquid diluent 42 to rupture weakened sections 24 in container dividing seal 22 as shown in FIG. 4. Powdered medicament 44, now exposed by the removal of stoppers 32 and 34 from vial 30, is in fluid communication with liquid diluent 42 which has now flowed into second compartment 26 from first compartment 28 by passing through now ruptured weakened sections 24 as shown by arrows "F" in FIG. 4. Further manipulation by compressing the walls of first compartment 28 agitates liquid diluent 42 and causes further mixing of the liquid diluent 42 and the powdered medicament 44. Once the diluent and medicament are mixed, further additions or samplings may be made through additive port 38 and when ready, the diluent-medicament mixture may be dispensed through administration port 40.

Operation of the first alternative embodiment of the device 110 shown in FIG. 5 is similar to that of the preferred embodiment 10. Rather than breaking weakwelds 24 in the container dividing seal 22 as in the preferred embodiment 10, stoppers 132 and 134 are removed by utilizing the flexibility of thermoplastic sheets 118 and 120. This removal of stoppers 132 and 134 from vial 130 exposes powdered medicament 144 to liquid diluent 142. As in the preferred embodiment, the flexible walls 118 and 120 of container 112 may be compressed to better effect intermixing of liquid diluent 142 and powdered medicament 144 by a flow through or flushing action of vial 130.

Operation of the second alternative embodiment of the device of the present invention 210 shown in FIG. 7 is substantially the same as the operation of the preferred embodiment 10. In embodiment 210 the manipulation of the flexible sides of the second compartment 226 of container 212 is used both to effect removal of stoppers 232 and 234 and separate connecting stopper 233 to separate from vial sections 230 and 231. This system allows two separate medicaments 244 and 245 to be added to liquid diluent 242.

Operation of the third alternative embodiment of the device 310 of the present invention shown in FIG. 8 is also substantially the same as the operation of the preferred embodiment 10. In embodiment 310 hydraulic forces developed within liquid diluent 342 must first rupture weakened sections 325 in first dividing partitions 323 before passing through the central or test zone 327 and being used to rupture weakened sections 324 in second dividing partition 322. The presence of moisture or any medicament in central or test zone 327 before mixing provides an indication to the user that the moisture barrier between liquid diluent 342 and medicament 344 may have been compromised during packaging, handling or storage of container and mixing system 310.

In the preferred embodiment and in the other embodiments the preferred material for manufacturing the flexible container 12 of this invention is a translucent polyester or a polypropylene plastic. However, other resinous materials such as polyvinylchloride or polyethylene may be used. Stoppers 32 and 34 may be fabricated from rubber; however, a flexible thermoplastic resin may be used in place of rubber. Vial 30 is typically made of glass; however, a rigid or semirigid plastic such as polypropylene or polycarbonate compatible with the stored medicament may be substituted for glass.

Seals between plastic sheets may be made using heat, RF techniques or any other suitable method. Weakened sections in the seals are formed by reducing the width of the seal die so that upon the application of force to the flexible container the weakened portion of the seal will come apart while other wider seals remain intact.

While the present dual compartmented container has been preferably described in the preferred and alternative embodiments for use with a powdered medicament in a vial and liquid diluent in the first compartment, the mixing system is usable with a wide variety of incompatible materials. For example, a liquid could be placed both in the stoppered vial and in the first compartment.

Further, while the present dual compartmented container has been described for use with fluid materials in the health care field, it will be appreciated that the container can be used in other fields. For example, it would have application with any type of fluid materials where it is necessary to store the two incompatible materials separately until just prior to mixing and use. It should be understood that the word "fluid" as employed in this specification or claims is meant to imply any material which will flow from one container to another, whether a liquid, solid or gas.

It will be seen that through the present invention there is now provided a manually operable, container and mixing system which is easily manufactured and used. The inexpensive container and mixing system of this invention also affords a sterile environment for isolation of fluid materials during packaging, storage and prior to mixing. Once the materials are mixed the container system becomes a convenient supply source in an I.V. administration system.

The foregoing invention can now be practiced by those skilled in the art. Such skilled persons will know that the invention is not necessarily restricted to the particular embodiments described herein. The scope of the invention is to be defined by the terms of the appended claims, which are given meaning by the preceding description.

What is claimed is:

1. A device for separately storing and subsequently mixing a fluid and a medicament comprising:

a flexible sealed container having at least one port;

partition means for dividing said flexible container, said partition means spanning the interior of said flexible container to define first and second compartments within said flexible container, said partition means having at least one weakened section for providing communication between said first and second compartments upon severing of the weakened section;

said first compartment being sealed for storing the fluid therein and being in fluid communication with said port;

a vial having a medicament therein and having at least one opening and a removable barrier closing said opening, said vial disposed within said second compartment;

whereby mixing of the fluid and the medicament is accomplished by manipulation of said second compartment of said flexible container to remove said removable barrier from said vial and by manipulation of the walls of the flexible container to cause severing of the weakened section of said partition means, allowing the fluid to commingle with the medicament.

2. The device as defined in claim 2 wherein said partition means is formed by sealing together the opposing walls of said flexible container.

3. The device as defined in claim 1 wherein said second compartment contains a plurality of vials.

4. The device as defined in claim 1 wherein said vial is made of glass.

5. The device as defined in claim 1 further including means to retain said vial against the side of said flexible container.

6. The device as defined in claim 1 wherein said first compartment of said flexible container includes a plurality of ports.

7. The device as defined in claim 6 wherein one of said ports is adapted to receive means for the passage of fluid into an I.V. administration set.

8. The device as defined in claim 1 wherein said vial contains a powder or liquid medicament and said first compartment contains a liquid diluent.

9. The device as defined in claim 1 wherein said vial is an assembly divided into two vial sections connected by a removable stopper, said vial sections constructed and arranged to enable said stopper to be removed from said sections by manipulation of said flexible container.

10. The device of claim 1, wherein said vial includes a hollow body having an opening at each end and a removable barrier closing each said opening.

11. The device of claim 1, wherein said removable barrier is a removable stopper.

12. A device for separately storing and subsequently mixing a fluid and a medicament comprising:

a flexible sealed container having at least one port;

first and second partition means for dividing said flexible container, said first and second partition means spanning the interior of said flexible container to define first, second and central sealed compartments within said flexible container with said central compartment between said first and second compartments, said first partition means being disposed between said first and central compartments and having at least one weakened section for providing communication between said first and central compartments upon severing of the weakened section, said second partition means being disposed between said central and second compartments and having at least one weakened section for providing communication between said central and second compartments upon severing of the weakened section, said first compartment containing said fluid during storage and being in fluid communication with said port;

a vial having a medicament therein and having at least one opening and a removable barrier closing said opening, said vial disposed within said second compartment;

whereby mixing of the fluid and the medicament is accomplished by manipulation of said second compartment of said flexible container to remove said removable barrier from said vial and by manipulation of the walls of the flexible container to cause severing of the weakened sections of said first and second partition means, allowing the fluid to commingle with the medicament.

13. The device as defined in claim 12 wherein said partition means is formed by sealing together of the opposing walls of said flexible container.

14. The device of claim 12, wherein said vial includes a hollow body having an opening at each end and a removable barrier closing each said opening.

15. The device of claim 12, wherein said removable barrier is a removable stopper.

16. A device for separately storing and subsequently mixing a fluid and a medicament comprising:

a flexible container defining a sealed compartment having a fluid therein and having at least one port;

a vial having a medicament contained therein and comprising a hollow body having an opening at each end and a removable barrier closing each said opening; said vial, including said openings and barriers, contained within the confines of said sealed compartment;

whereby mixing of the fluid and the medicament in the vial is accomplished by first manipulating said flexible container to remove said barriers from each said opening of the vial within said compartment, then manipulating the walls of said flexible container to effect flushing of the vial and intermixing of the fluid and the medicament.

17. The device of claim 16, wherein said removable barriers comprise removable stoppers.

* * * * *